United States Patent [19]

Beers et al.

[11] Patent Number: 4,735,979

[45] Date of Patent: Apr. 5, 1988

[54] AUTO-ADHERING ONE-COMPONENT RTV SILICONE SEALANT COMPOSITION UTILIZING AN ADHESION PROMOTER

[75] Inventors: M. Dale Beers, Aurora; James E. Thompson, Lakewood, both of Ohio

[73] Assignee: Loctite Corporation, Newington, Conn.

[21] Appl. No.: 719,751

[22] Filed: Apr. 4, 1985

[51] Int. Cl.$^4$ ............................................. C08K 5/54
[52] U.S. Cl. ...................................... 524/188; 524/730; 524/785; 524/788; 524/860; 556/421; 528/17; 528/18; 528/33; 528/34; 528/901
[58] Field of Search ............... 556/421; 528/17, 18, 528/33, 34, 901; 524/730, 860, 188, 785, 788

[56] References Cited

U.S. PATENT DOCUMENTS

| | | | |
|---|---|---|---|
| 3,035,016 | 5/1962 | Bruner | 260/46.5 |
| 3,133,891 | 5/1964 | Ceyzeriat | 260/18 |
| 3,185,576 | 6/1965 | Sweet | 260/46.5 |
| 3,208,971 | 9/1965 | Gilkey | 260/46.5 |
| 3,382,205 | 5/1968 | Beers | 260/37 |
| 3,517,001 | 6/1970 | Berger | 260/248 |
| 3,541,044 | 11/1970 | Beers et al. | 260/37 |
| 3,776,933 | 12/1973 | Toporcer | 260/448.2 |
| 3,837,878 | 9/1974 | Beers | 106/308 Q |
| 3,847,848 | 11/1974 | Beers | 260/18 |
| 3,927,042 | 12/1975 | Golitz | 260/348 |
| 3,962,160 | 6/1976 | Beers et al. | 260/18 |
| 4,100,129 | 7/1978 | Beers | 260/37 |
| 4,323,489 | 4/1982 | Beers | 524/788 |
| 4,356,116 | 10/1982 | Beers | 524/837 |
| 4,395,526 | 7/1983 | White et al. | 528/18 |
| 4,506,058 | 3/1985 | Ashby et al. | 524/730 |

FOREIGN PATENT DOCUMENTS 2548200 6/1983 France.

*Primary Examiner*—Melvyn I. Marquis
*Attorney, Agent, or Firm*—Vidas & Arrett

[57] ABSTRACT

An auto-adhering one-component room temperature vulcanizable silicone sealant composition generally utilizing a di-substituted mixed oxime-alkoxysilyalkyl area adhesion promoter compound. The sealant has low odor, is non-corrosive to ferrous or aluminum substrates, has good adhesion to many types of substrates, and eliminates the need for a silicone resin primer. In addition, it exhibits surprisingly good adhesion to oil contaminated surfaces.

9 Claims, No Drawings

AUTO-ADHERING ONE-COMPONENT RTV SILICONE SEALANT COMPOSITION UTILIZING AN ADHESION PROMOTER

TECHNICAL FIELD

The present invention relates to an auto-adhering one-component RTV silicone sealant. More specifically, the present invention relates to the utilization of a di-substituted mixed oxime-alkoxysilylakyl urea compound as an adhesion promoter in the sealant.

BACKGROUND

Heretofore, low modulus characteristics of silicone rubbers have been desirable in accommodating joint movement due to vibration and thermal cycling since less stress is exerted on sealant-metal bond interface. Such low modulus properties generally decrease the probability of oil leaks. However, oil resistance has been traditionally improved by utilizing comparatively high crosslink densitites. The result was lower elongation properties and, hence, reduced movement capabilities. When fewer crosslinks were incorporated into the elastomer to lower the modulus, generally more rapid deterioration of the polymer backbone by nucleophilic or electrophilic agents occurred at elevated temperatures. Accordingly, room temperature vulcanizable elastomers having good oil resistance were generally not made.

U.S. Pat. No. 3,189,576 to Sweet relates to oxime curatives and to new organosilicon intermediates.

U.S. Pat. No. 4,323,489 as well as U.S. Pat. No. 3,962,160, both to Beers, generally relate to oxime curable room temperature vulcanizates. More specifically, the '489 patent relates to a vulcanizable silicone rubber composition with very low modulus containing a silanol end-stopped diorganopolysiloxane, a difunctional acetamide coupler as a chain extender and a minor amount of a compound containing an oxime functionality thereon as a trifunctional crosslinker.

U.S. Pat. No. 4,356,116 to Beers relates to a low volatile room temperature vulcanizable silicone rubber composition containing various components including a silanol polymer, a crosslinking agent, and a filler.

U.S. Pat. No. 3,517,001 to Berger relates to adhesion promoter compositions.

U.S. Pat. No. 4,100,129 to Beers also relates to adhesion promoter compositions curable in the presence of moisture.

U.S. Pat. No. 4,395,526 to White et al relates to a stable, substantially acid-free, one-component curable polyalkoxy-terminated organpolysiloxane composition having a condensation catalyst, such as a tin compound. The material in this patent also serves as an adhesion promoter.

Specific patents relating to acetoxy curing room temperature vulcanizable silicones include Ceyzeriat, U.S. Pat. No. 3,133,891, Brunner, U.S. Pat. No. 3,035,016, and Beers, U.S. Pat. No. 3,382,205. More specifically, the Beers' patent relates to organopolysiloxane compositions comprising a mixture of organotriacyloxysilane and a base mixture containing organosiloxane having chemically combined organsiloxy units.

U.S. Pat. No. 3,541,044 to Beers relates to a substantially anhydrous organopolysiloxane composition curable to the elastomeric state upon exposure to moisture. Another patent by Beers, namely U.S. Pat. No. 3,837,878 relates to a two-component room temperature vulcanizable silicone rubber composition suitable for molding applications whereas U.S. Pat. No. 3,837,878 also to Beers relates to a process for treating silicone fillers.

U.S. Pat. No. 3,776,933 to Toporcerer relates to chain extenders with regard to RTV systems.

While most of the above patents do relate to organopolysiloxane compositions, they do not teach one-component room temperature vulcanizable silicone sealant composition of the present invention or a di-substituted mixed oxime-alkoxysilylalkyl urea derivative as an adhesion promoter.

DISCLOSURE OF INVENTION

It is therefore an aspect of the present invention to provide an adhesion promoter.

It is yet a further aspect of the present invention to provide an adhesion promoter as above, wherein said adhesion promoter can be made via the reaction product of an alkoxysilylalkylamine.

It is another aspect of the present invention to provide an auto-adhering one-component room temperature vulcanizable silicone sealant containing an adhesion promoter which sealant is non-corrosive with regard to iron containing and aluminum substrates.

It is still another aspect of the present invention to provide an auto-adhering one-component room temperature vulcanizable silicone sealant containing an adhesion promoter as above, wherein no primer is required to be initially applied to said substrate.

It is yet another aspect of the present invention to provide a sealant which will bond to oil contaminated surfaces.

The compositions of the present invention generally exhibit outstanding auto-adhering adhesion even an oil contaminated metals such as the aluminum and steel surfaces encountered in the auto industry. These compositions also have excellent oil-resistant properties including oil resistance at elevated temperatures, for example 300° F., and are particularly useful as silicone formed-in-place gasketing.

An auto-adhering one-component room temperature vulcanizable silicone sealant compound of the present invention has an adhesion promoter of the following formula:

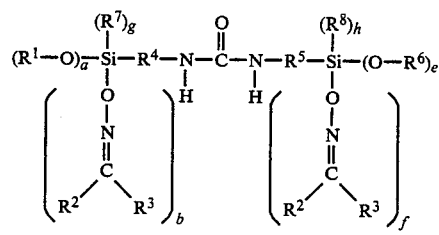

$R^1$ and $R^6$ are independently a non-aromatic hydrocarbyl or halo substituted hydrocarbyl group or a carboxyalkyl group having 1 to 10 carbon atoms. $R^2$, $R^3$, $R^7$ and $R^8$ are independently H, hydrocarbyl or halohydrocarbyl, either of which may be aromatic or non-aromatic, or carboxyalkyl having 1 to 10 carbon atoms. $R^4$ and $R^5$ are divalent hydrocarbon or halohydrocarbon groups of 1 to 20 carbon atoms, suitably 1 to 10 carbon atoms.

The non-aromatic hydrocarbyl groups may be aliphatic or cycloaliphatic, saturated or unsaturated groups including alkyl, alkenyl, alkynyl, cycloalkyl etc. Aromatic hydrocarbyl groups include aliphatic substituted aromatic and aromatic substituted aliphatic groups.

$R^1$ and $R^6$ are preferably methyl or ethyl. $R^2$ and $R^3$ are preferably alkyl such as methyl or ethyl.

$R^4$ and $R^5$ are preferably $C_3$-$C_8$ alkylene groups. $R^7$ and $R^8$ are desirably alkyl such as methyl or ethyl. Preferably $R^7$ and $R^8$ are hydrogen.

The numerals designated by a, b, f, and e, are independently 0–3; g and h are 0 or 1; and $a+b+g=f+e+h=3$. Suitably b and f are 1 to 3. Preferably a and e are 1, b and f are 2 and g and h are 0.

Examples of specific adhesion promoters include the following:

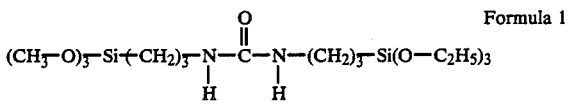
Formula 1

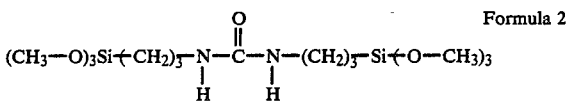
Formula 2

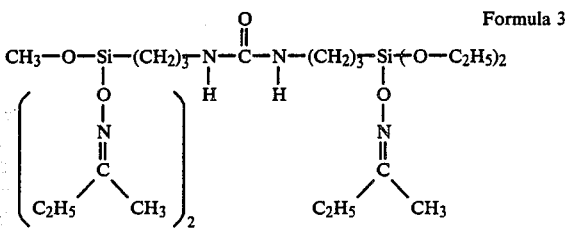
Formula 3

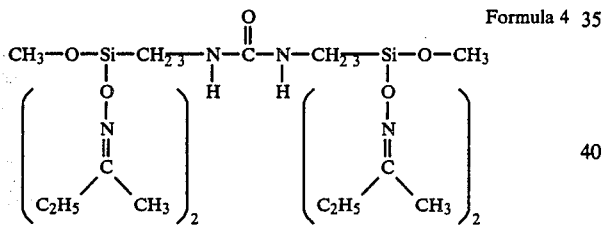
Formula 4

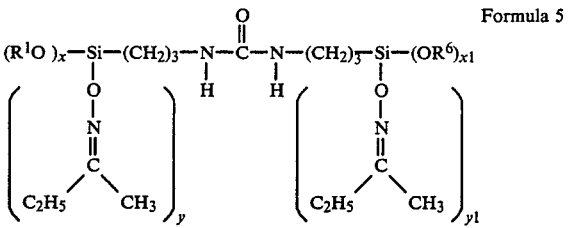
Formula 5

Where x = 0 to 3
Where y = 0 to 3
$x + y = x^1 + y^1 = 3$
$x^1 = 0$ to 3
$y^1 = 0$ to 3

The actual adhesion promoter often is a statistical mixture of the above formulations and/or of the "general formula" set forth above. Whenever formula 1 or 2 is utilized, it is desirable that a compound of formulas 3 through 5 also be utilized so that a more reactive oxime group exists.

When the various end segments, that is $(R'O)_a$ and $(OR^6)_e$ are different, for example, $(R'O)_a$ is trimethoxy and $(OR^6)_e$ is triethoxy, the adhesion promoter is a liquid. In other words, unsymmetrical end groups yield a liquid. Thus, it was thought that when the end groups are symmetrical, the adhesion promoter would also be a liquid. However, when symmetrical end segments or groups such as triethoxy were utilized, the promoter unexpectedly was a solid. This is truly an unexpected result since the end group segments constitute a very small portion of the structure. Inasmuch as liquids are easier to handle, unsymmetrical end segments or groups are preferred.

The adhesion promoter of the present invention can be made in a number of different ways. A desired mode of preparation involves reacting a compound of Formula A with Formula B.

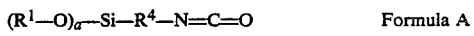
Formula A

Formula B $R^1$, $R^4$, $R^5$, $R^6$ as well as a and e are set forth above. The reaction is exothermic and spontaneous upon mixing the two (2) ingredients together. The reaction is generally carried out in the presence of an inert gas blanket such as nitrogen to avoid reaction of the compound with moisture.

Generally, from about 0.95 to about 1.0 moles of Formula B is utilized per mole of Formula A with an equal molar ratio being preferred although much larger or smaller amounts can be utilized. The reaction is carried out at atmospheric pressure at a temperature of from about 40° C. to about 100° C. Formula (B) is slowly added to (A) while stirring in a 3 neck flask equipped with a thermometer and blanketed with nitrogen.

Reaction of a compound of Formulas A and B results in a compound of Formula C.

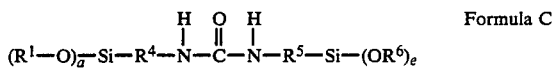
Formula C

The oxime crosslinking units can be grafted to the compound of Formula C by heating with an oxime compound at a temperature of from about 45° C. to about 150° C., preferably from about 50° C. to about 120° C. being preferred. Once again, an inert gas blanket, for example nitrogen, is utilized to avoid reaction with moisture. The type of oxime compounds utilized are generally oxime crosslinkers set forth in Formulas Type I and Type II or mixtures thereof.

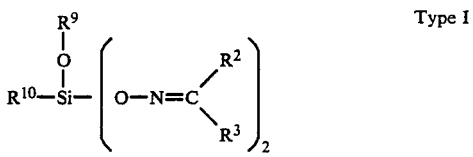
Type I or

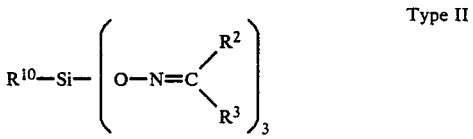
Type II $R^{10}$ is generally an alkyl having from 1 to 8 carbon atoms with methyl being preferred, an alkenyl having from 2 to 8 carbon atoms with vinyl being preferred, a haloalkyl having from one to eight carbon atoms, a trifluoralkyl having from one to eight carbon atoms, or a haloalkyenyl having from two to eight carbon atoms.

$R^9$ is a hydrocarbyl, a halohydrocarbyl, or a carboxyalkyl having from 1 to 10 carbon atoms, preferably $R^9$ is methyl or ethyl.

Preparation of the oxime compounds set forth in the Type I and Type II formulae is generally well known to the art as set forth in U.S. Pat. No. 3,189,576, which is hereby fully incorporated by reference as to the preparation thereof.

Generally, the greater the number of oxime groups on the silicon atom of the adhesion promoter the better the adhesion. Adhesion is also effected by the R group on the crosslinker. It is particularly enhanced when such a group is alkenyl. Oftentime, the oxime type crosslinker utilized to make the silicone sealant of the present invention can be a mixture. That is, from about 5 percent to about 40 percent and preferably from about 10 percent to about 20 percent by weight of an oxime compound having the formulation of the Type I oxime can be utilized based upon the total weight of oxime compounds in the entire formulation. Similarly, from about 60 to about 95 percent, and preferably from about 80 to about 90 percent of a Type II oxime can be utilized based upon the total weight of all oxime compounds in the composition. Considered on a molar basis, from about 0.05 moles to about 0.4 moles of the Type I oxime, and preferably from about 0.1 to about 0.2 moles is utilized per 1 mole of Type I and II oxime compound.

Considering the sealant composition of the present invention, it contains a silanol terminated diorganosiloxane polymer as the basic ingredient. This linear polymer may be devolatilized in a manner such as set forth in U.S. Pat. No. 4,356,116 and generally has a viscosity of from about 2,000 to about 250,000 centipoise at 25° C. and preferably from about 10,000 to about 120,000 centipoise. The polymer has the formula

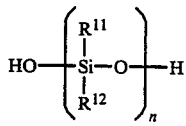

where n is from about 300 to about 1,000, where $R^{11}$ and $R^{12}$ can be the same or different, where $R^{11}$ and $R^{12}$ is an alkyl group having from 1 to 8 carbon atoms with methyl being preferred, a cycloalkyl group having from 4 to 7 carbon atoms such as cyclohexyl, an alkenyl group having from 2 to 8 carbon atoms with vinyl being preferred, an aryl or an alkyl substituted aryl group having from 6 to 14 carbon atoms such as phenyl, methylphenyl, or a fluoralkyl group having from one to eight carbon atoms with 3,3,3-trifluoropropyl being preferred. The amount of the linear polymer generally ranges from about 25 to about 90 percent by weight and preferably from 30 to about 60 percent by weight based upon the total weight of the low modulus RTV silicone composition. Such polymers are commercially available and are manufactured by Mobay, Union Carbide and Wacker Chemie.

The sealant composition further comprises the adhesion promoter of the invention, which may be mixed with oxime crosslinking agents, and optionally a plasticizer.

In order to insure that gellation or viscosity increases do not occur, an excess of the adhesion promoter containing the oxime crosslinking agents to the silanol in the base polymer is utilized at a ratio of from about 1.2 to about 4.0 with from about 2.0 to about 3.0 being preferred, molar ratio of crosslinker to silanol groups.

Considering the adhesion promoter, the amount thereof is from about 0.5 to about 3 percent by weight with from about 0.8 to about 2 percent by weight being preferred based upon the total weight of the sealant composition.

An organo tin catalyst is desirably utilized in the composition to promote reaction of the oxime compounds and silicone polymer. The amount of said catalyst is generally from about 0.01 to about 0.5 percent by weight and preferably from about 0.02 to about 0.2 percent by weight based upon the total weight of the sealant composition.

Examples of organo tin catalysts are well known to the art and include those set forth in U.S. Pat. Nos. 4,356,116 and 4,395,526, hereby fully incorporated by reference. Examples of specific tin compounds include disbutyltindilaurate, dibutyltindiacetate, tin octoate, dimethyltindibutyrate, triethyltintartrate, tin oleate, dibutyltinoxide, and dimethyltinbisneodecanoate, and the like.

The plasticizer utilized along with the linear base polymer in the sealant composition is a devolatilized triorganosiloxy terminated with diorganopolysiloxane fluid existing in an amount of from 0 to 1 to about 40 percent by weight and desirably from 5 to about 25 twenty-five percent by weight based upon the total siloxane composition. The plasticizer lowers the durometer and modulus of the cured rubber and, lowers the viscosity of the overall system or composition. However, the viscosity of the plasticizer should not be too low in as much as it will tend to bleed out of the composition. Accordingly, the viscosity generally ranges from about 50 to 100,000 centipoise and preferably from about 500 to about 10,000 centipoise.

The plasticizer is a diorganopolysiloxane polymer terminated with monofunctional, triorgano siloxy end groups. The organo compounds within the repeating units are the same as $R^{11}$ and $R^{12}$ set forth herein above with regard to the base polymer. However, it may contain trace quantities of trifunctional monoorganosiloxy units originating from impurities in the starting materials. The siloxy units contain an alkyl group having from 1 to 8 carbon atoms with methyl being preferred. The number of repeating units in the plasticizer is generally from about 20 to about 900. As with the linear base polymer, the plasticizer is devolatilized in accordance with any conventional manner or process, well known to the art. A specific example of devolatilization is set forth in U.S. Pat. No. 4,356,116 which is hereby fully incorporated by reference.

In order to reinforce the polymer network as well as to impart non-sag properties to the system, a thixotropic agent is added to the overall composition. This agent which also adds physical strength to the system desirably is a treated fumed silica filler being preferred. Treated silica fillers generally have lower moisture content, and result in better low modulus properties. The amount of silica filler generally ranges from about 1 to about 20 percent by weight and from about 3 to about 8 percent by weight being preferred. Treated or untreated silica fillers are well known to the art and generally any such conventional filler can be utilized. Examples of specific silica fillers are set forth in U.S. Pat. No. 3,837,878 which is hereby fully incorporated by reference. Additionally, treated silica as set forth in Lucas U.S. Pat. No. 2,938,009, Lichtenwalner U.S. Pat. No. 3,004,859, and Smith U.S. Pat. No. 3,635,743, all hereby fully incorporated by reference, can be utilized. Typically, the silica filler has a very high surface area such as about 200 $M^2$/gram.

Optionally, from about 0.1 to about 5 percent by weight and preferably from about 0.2 to about 3 percent by weight based upon the total weight of the overall system or composition of a thermal aging additive can be utilized. This optional component functions to reduce oxidation and thermal rearrangement of polymers at elevated temperatures. These antioxidants may include materials like cerium neodencanoate, rare earth octoates and iron octoate. Representative samples can also include thermal aging additives such as carbon black, iron oxide powder, and titanium dioxide. Naturally, other pigments can be utilized to impart various desired colors.

Another optional ingredient is an inert semi or non-reinforcing filler such as ground quartz, calcium carbonate, talc, clay, various silicate compounds and other materials or their treated counterparts well known in the art. The amount utilized is from about 5 percent to about 60 percent by weight based upon the total weight of the sealant composition.

The silicone sealants of the present invention are useful in that they cure at room temperature. Moreover, the need for applying a primer precoat to a substrate to obtain good adhesion is also eliminated. The silicone sealants moreover have a low odor and give good adhesion to various substrates such as glass, ceramics, various metals such as aluminum, steel and the like, as well as various plastics, such as acrylates, fiberglass reinforced polyesters and acrylonitrile-butadiene-styrene terpolymers. The sealants also exhibit excellent oil resistance at elevated temperatures of about 300° F. Thus, such sealants find use wherever such properties are desired. Specific examples of utility include RTV silicone adhesives, as for examples, gaskets, bath tub caulking compounds, masonry joint materials, plastic adhesives, and the like. A desired use is an automobile engine sealants as for example, valve cover gaskets, oil pan gaskets, and the like.

The preparation and incorporation of the aforementioned silane adhesion promoter into a silicone sealant composition can be accomplished according to one of two modes: The first mode involves a reaction product of various oxime type compounds and thus the exact end product is a mixture while in the second mode, a specific oxime product is produced.

In the first mode of preparation about 0.5 to 4 parts of an equimolar mixture of a compound of prereacted Formula A and a compound of Formula B is prepared by mixing under dry nitrogen for about one hour to up to 60° C. is added to the crosslinker mixture consisting of about 12 parts of the oxime curing agent set forth above and 0.2 parts of an organotin salt catalyst as also set forth above and this mixture is heated at 50° C. for 10 to 20 hours in a closed container.

The silicone sealant compounds is then prepared by charging the various ingredients into a mixture under dry conditions as through the use of dry nitrogen to prevent hydrolysis of the oxime crosslinking compound. Generally, the polymer is added first with the plasticizer. The oxime composition is mixed under high speed or agitation as well as under a vacuum for several minutes or even hours to remove the entrapped nitrogen bubbles. The resulting paste formed can be placed or extruded into a desirable container and the like.

The invention will be better understood by reference to the following example:

EXAMPLE 1

| | | Weight % |
|---|---|---|
| 1. | 10,000 cps, viscosity silanol terminated polydimethylsiloxane | 40.06 |
| 2. | 1000 cps trimethylsilyl terminated polydimethylsiloxane | 15.46 |
| 3. | Stearic acid treated calcium carbonate | 34.05 |
| 4. | Polydimethylsiloxane treated fumed silica having a surface area of approximately 200 $m^2$/gram | 3.61 |
| 5. | Iron oxide | 1.40 |
| 6. | Methyltris-methylethylketoximosilane | 4.81 |
| 7. | Dimethyltinbisneodecanoate | 0.08 |
| 8. | Equimolar mixture of gamma isocyanato propyl trimethoxy silane and gamma aminopropyl triethoxysilane | 0.53 |

This composition was prepared by charging the ingredients into the mixing can of a vertical laboratory change can mixer which had been flushed with dry nitrogen to prevent the hydrolysis of the oxime crosslinker and adhesion promoter.

Ingredients (6), (7) and (8) were heated in a closed glass jar in a 50° C. oven for 16 hours and allowed to cool before incorporation into the sealant formulation. The ingredients were subsequently added as follows: (1), (2), (3), (4), (5), then the mixture of (6), (7) and (8). Then mixed at high speed under vacuum for approximately two hours and afterwards the resulting paste was transferred to a pressure Semco mixer. It was then extruded from the pressure Semco into six ounce polyethylene cartridges.

It was found that the 180° C. peel adhesion of this sealant to alclad aluminum after curing for 14 days was 12 to 13 pounds per linear inch with 100% cohesive failure versus 0 to 2 pounds per linear inch with 100% adhesive failure for a sealant without (8).

In the second mode of preparation an equimolar mixture of a compound of formula A and a compound of formula B are allowed to react at room temperature and atmospheric pressure preferably under an inert gas blanket and a sufficient amount of a ketoxime compound such as methylethylketoxime is added to the reaction product and the mixture heated to cause partial substitution of ketoxime on the silicon atom by displacement of the alkoxy moieties. The sealant is then prepared as in the first mode of preparation.

This mode of preparation can be better understood by reference to the following examples:

EXAMPLE 2

44.2 g (0.2 moles) of gamma aminopropyl triethoxysilane was added dropwise to 41.0 g (0.2 mole) of gamme isocyanatopropyl trimethoxysilane at room temperature and atmospheric pressure under a nitrogen blanket. The addition was done slowly to avoid excessive heat build-up from the reaction exotherm. When the addition was complete 38.3 g (0.44 mole) of methyl ethylketoxime was added to the reaction product and the mixture was heated to 120° C. for about 4 hours. The resulting analysis by gas chromatograph indicated a mixture of the substitution products of methylethyl ketoximo moieties on the silicon atom.

EXAMPLE 3

|   |   | Weight % |
|---|---|---|
| 1. | 10,000 cps. viscosity silanol terminated polydimethylsiloxane | 40.06 |
| 2. | 1000 cps trimethylsilyl terminated polydimethylsiloxane | 15.46 |
| 3. | Stearic acid treated calcium carbonate | 34.05 |
| 4. | Polydimethylsiloxane treated fumed silica having a surface area of approximately 200 m²/gram | 3.61 |
| 5. | Iron oxide | 1.40 |
| 6. | Methyltris-methylethylketoximosilane | 4.81 |
| 7. | Dimethyltinbisneodecanoate | 0.08 |
| 8. | The material of example 2 | 0.53 |

This composition was prepared as in Example 1. The ingredients were added in the order: (1), (2), (3), (4), (5), (6), (7), and (8), then mixed at high speed under vacuum for approximately two hours and afterward the resulting paste was transferred to a pressure Semco mixer and extruded into six ounce polyethylene cartridges. The peel adhesion of this sealant to Alclad aluminum after curing for four weeks was 23 pli with 100% cohesive failure.

Accordingly, it can be seen that a significant increase in adhesion occurs utilizing the adhesion promoter of the present invention.

Examples Demonstrating the Utility of Mixed Oxime Alkoxy Silyalkyl Urea Adhesion Promoters

EXAMPLE 4

| (1) | 80,000 cps. viscosity silanol terminated polydimethylsiloxane | 39.81 |
|---|---|---|
| (2) | 1000 cps. trimethylsilyl terminated polydimethylsiloxane | 15.36 |
| (3) | Stearic acid treated calcium carborate | 33.83 |
| (4) | Raven 1020 carbon black | 1.07 |
| (5) | Polydimethylsiloxane treated fumed silica having a surface area of approximately 200 M²/gram | 3.58 |
| (6) | Vinyl tris-methylethylketoximo-silane | 4.78 |
| (7) | Dimethyltinbis-neodecanoate | 0.08 |
| (8) | N—(3-trimethoxysilylpropyl)-N'—(3-triethoxysiylpropyl)urea | 1.49 |

The above composition was prepared by charging the following ingredients to the mixer under dry nitrogen to prevent hydrolysis. (1) was added to the mixer followed by (6), (3), (4), (5), (2), (8) and (7).

The resulting paste was then made into ASTM sheets. The test sheets were then allowed to cure for seven days. The initial cured and two week oil immersion properties were then determined. The oil immersion tests were performed after two weeks (14 days) at 300° F. in 5W-30 engine fill oil (CITGO grade). The data is summarized below.

|   | Initial | Two Weeks at 300° F. in 5W-30 CITGO Oil |
|---|---|---|
| Shore A, hardness | 28 | 16 |
| Tensile, psi |   |   |
| at 50% extension | 41 | — |
| at 75% extention | 51 | — |
| at 100% extension | 65 | — |
| at ultimate | 196 | 137 |
| Elongation, % | 520 | 470 |
| Volume swell, % | — | 27 |

Adhesion test specimens were also prepared using aluminum and steel panels which had previously been contaminated with thin films fo 5W-30 engine oil. These were then allowed to cure for two weeks at room temperature. It was noted that cohesive failure (failure within the rubber) was obtained in each case. In compounds where the adhesion promoter was left out, adhesive failure (failure from the metal substrate) was noted. Adhesion on oil contaminated surfaces is an obvious advantage in maintaining an oil leak-free seal on automotive engine flanges.

It should be noted that the adhesion promoter was not pre-equilibrated with the oxime crosslinker in the above example.

EXAMPLE 5

Example 4 was repeated except that the polydimethylsiloxane treated fumed silica level was increased from 3.58 to 5.09 weight percent. The following performance properties were measured.

|   | Initial | Two Weeks at 300° F. in 5W-30 CITGO Oil |
|---|---|---|
| Shore A, hardness | 31 | 22 |
| Tensile, psi |   |   |
| at 50% extension | 51 | — |
| at 75% extention | 65 | — |
| at 100% extension | 79 | — |
| at ultimate | 211 | 168 |
| Elongation, % | 490 | 530 |
| Volume swell, % | — | 27 |

Again, the same excellent adhesion results were obtained.

While in accordance with the patent statutes, the best mode and preferred embodiment have been described in detail, the scope of the invention is not be limited thereto, but rather limited by the scope of the attached claims:

What is claimed is:

1. A room temperature vulcanizable silicone rubber composition comprising:
   from about 25 to 90 percent by weight based upon the total weight of the composition of a devolatilized silanol terminated diorgano-siloxane base polymer having a viscosity from about 2,000 to about 250,000 centipoises at 25° C. wherein said organo groups are the same or different and are selected from the group consisting of an alkyl having from 1 to 8 carbon atoms, a cycloalkyl having from 4 to 7 carbon atoms, an alkenyl having from 2 to 8 carbon atoms, an aryl or an alkyl substituted aryl having from 6 to 14 carbon atoms, and a fluoroalkyl having from 1 to 8 carbon atoms;

from about 0 to about 40 percent by weight based upon the total weight of said composition of a devolatilized diorganopolysiloxane fluid plasticizer terminated with triorganosiloxy groups, said organo groups selected from the group consisting of alkyl having 1 to 8 carbon atoms, cycloalkyl having 4 to 7 carbon atoms, alkenyl having 2 to 8 carbon atoms, aryl or alkyl substituted aryl having 6 to 14 carbon atoms and fluoroalkyl having 1 to 8 carbon atoms said plasticizer having a viscosity from about 50 to about 100,000 centipoises at 25° C.; and 0.5 to 3 percent by weight of an adhesion promoter of the formula:

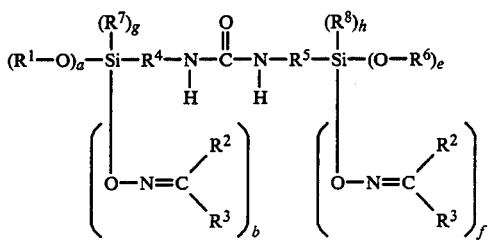

wherein $R^1$ and $R^6$ are independently non-aromatic hydrocarbyl or halohydrocarbyl groups or carboxyalkyl groups having 1 to 10 carbon atoms; $R^2$, $R^3$, $R^7$ and $R^8$ are independently H, hydrocarbyl, halohydrocarbyl or carboxyalkyl having 1 to 10 carbon atoms; $R^4$ and $R^5$ are divalent hydrocarbyl or halohydrocarbyl groups of 1 to 10 carbon atoms; a and e are 0 to 2; b and f are 1 to 3; q and h are 0 or 1 and $a+b+g=f+e+h=3$.

2. A composition as in claim 1 where g and h are 0.

3. A composition as in claim 2 where $R^1$ and $R^6$ are methyl or ethyl.

4. A composition as in claim 1 where $R^4$ and $R^5$ are $-(CH_2)_3-$.

5. The composition of claim 1 further comprising an effective amount of a thixotropic agent to impart non-sag properties to the composition.

6. A composition as in claim 1 further comprising an oxime crosslinking agent and an organotin catalyst.

7. A composition as in claim 6 wherein the said catalyst is present in an amount in the range of 0.01–0.5 percent based on total composition weight.

8. A composition as in claim 6 wherein the catalyst is selected from dibutyltin dilaurate; dibutyltin diacetate; tin octoate; dimethyltindibutyrate; triethyl tin tartrate; tin oleate; dibutyltin oxide and dimethyltinbis neodecanoate.

9. A composition as in claim 1 further comprising between 1% and 60% by weight of a filler.

* * * * *